(12) United States Patent
Nemeth et al.

(10) Patent No.: US 8,951,671 B1
(45) Date of Patent: Feb. 10, 2015

(54) TERNARY ALKALI-METAL AND TRANSITION METAL OR METALLOID ACETYLIDES AS ALKALI-METAL INTERCALATION ELECTRODES FOR BATTERIES

(71) Applicants: Karoly Nemeth, Darien (HU); George Srajer, Oak Park, IL (US); Katherine C. Harkay, Lemont, IL (US); Joseph Z. Terdik, Chicago, IL (US)

(72) Inventors: Karoly Nemeth, Darien (HU); George Srajer, Oak Park, IL (US); Katherine C. Harkay, Lemont, IL (US); Joseph Z. Terdik, Chicago, IL (US)

(73) Assignee: U.S. Department of Energy, Washington, DC (US)

( * ) Notice: Subject to any disclaimer, the term of this patent is extended or adjusted under 35 U.S.C. 154(b) by 0 days.

(21) Appl. No.: 13/688,631

(22) Filed: Nov. 29, 2012

(51) Int. Cl.
*H01M 4/60* (2006.01)
*C07F 19/00* (2006.01)

(52) U.S. Cl.
CPC ..................... *H01M 4/60* (2013.01)
USPC ............... 429/213; 423/440; 556/43; 556/46; 556/52; 556/58; 556/110; 556/121; 556/138

(58) Field of Classification Search
USPC ............. 252/500; 429/231.8, 231.95; 556/43, 556/46, 52, 58, 110, 121, 138
See application file for complete search history.

(56) References Cited

PUBLICATIONS

Uwe Ruschewitz, Z. Anorg.Allg.Chem., vol. 627, pp. 1231-1235 (2001).*
Cremer et al., Solid State Sciences, vol. 4, pp. 247-253 (2002).*

\* cited by examiner

*Primary Examiner* — Porfirio Nazario Gonzalez
(74) *Attorney, Agent, or Firm* — Joy Alwan; Brian J. Lally; John T. Lucas

(57) ABSTRACT

Novel intercalation electrode materials including ternary acetylides of chemical formula:

$A_nMC_2$ where A is alkali or alkaline-earth element; M is transition metal or metalloid element; $C_2$ is reference to the acetylide ion; n is an integer that is 0, 1, 2, 3 or 4 when A is alkali element and 0, 1, or 2 when A is alkaline-earth element. The alkali elements are Lithium (Li), Sodium (Na), Potassium (K), Rubidium (Rb), Cesium (Cs) and Francium (Fr). The alkaline-earth elements are Berilium (Be), Magnesium (Mg), Calcium (Ca), Strontium (Sr), Barium (Ba), and Radium (Ra). M is a transition metal that is any element in groups 3 through 12 inclusive on the Periodic Table of Elements (elements 21 (Sc) to element 30 (Zn)). In another exemplary embodiment, M is a metalloid element.

20 Claims, 6 Drawing Sheets

TERNARY ALKALI-METAL AND TRANSITION METAL OR METALLOID ACETYLIDES AS ALKALI-METAL INTERCALATION ELECTRODES FOR BATTERIES

STATEMENT REGARDING FEDERALLY SPONSORED RESEARCH OR DEVELOPMENT

The United States Government has rights in this invention pursuant to Contract No. DE-AC02-06CH11357 between the U.S. Department of Energy (DOE) and University of Chicago, Argonne LLC.

CROSS-REFERENCE TO RELATED APPLICATION(S)

The present non-provisional patent application/patent claims the benefit of priority of U.S. Provisional Patent Application No. 61/564,941, filed on Nov. 30, 2011, and entitled "LOW-WORKFUNCTION PHOTOCATHODES BASED ON ACETYLIDE COMPOUNDS," the contents of which are incorporated in full by reference herein.

FIELD OF THE INVENTION

Generally, the field of art of the present disclosure pertains to alkali cation intercalation electrodes for batteries based on ternary acetylides. Ternary acetylides are composed of three kinds of chemical elements and have the general formula of $A_nMC_2$, where A is alkali or alkaline-earth element; M is a transition metal or metalloid element; $C_2$ is reference to the acetylide ion ($C_2^{2-}$); n is an integer that is 0, 1, 2, 3 or 4 when A is an alkali element, and 0, 1, or 2 when A is an alkaline-earth element. Any possible combination of such ternary acetylides is also considered here for alkali cation intercalation electrode applications.

BACKGROUND OF THE INVENTION

Lithium ion (Li-ion) batteries are widely used from portable electric devices to electric cars. In these batteries, Li-ions intercalate primarily the anode material before discharge. During discharge they migrate from the anode through the electrolyte into the cathode, where they intercalate the cathode material. While Li-ions migrate from one electrode to the other, they change the oxidation number of the atoms in the electrodes they migrate from/to, as simultaneously with Li-ion migration, also electrons migrate from the anode to the cathode during discharge. Through these processes an electric circuit is operated with current flowing from the anode to the cathode in the electrolyte and from the cathode to the anode via the wire and load connecting the electrodes, during discharge. The driving force of the process is the chemical potential difference between the electrodes. Batteries operate until this potential difference fails to exist. During recharging this potential difference will be restored by an external power source.

Several intercalation materials are used as electrode components. Typically the anode (of the discharge) is made of graphite intercalating Li, the cathode (of the discharge) is made of transition metal compound ($LiFePO_4$, $LiCoO_2$, $LiMn_2O_4$, etc) nanocrystals embedded into a carbon matrix, the electrolyte is a non-aqueous liquid or polymer, and a membrane separates the anode and cathode spaces allowing for the passage of Li-ions only.

The performance of Li-ion batteries depends on the choice of the intercalation materials in the electrodes, and on the other components of the battery. Batteries that intercalate other than Li-ions are also known, for example in K-ion batteries (A. Eftekhari (2004), "Potassium Secondary Cell Based on Prussian Blue Cathode", Journal of Power Sources 126, 221) metal-organic frameworks do the intercalation in the cathodes during the discharge.

The use of ternary acetylides as Li-ion battery anode materials has been suggested in R. Pöttgen, et al. (2010), "Lithium-Transition Metal-Tetrelides—Structure and Lithium Mobility", Zeitschrift für Physikalische Chemie 224, 1475, even though only the use of $LiAgC_2$ and $LiAuC_2$ has been explicitly mentioned, as the only structurally characterized Li containing members of ternary acetylides at the time of the publication. $LiMC_2$ compounds would, however, be disadvantageous to be used as anode materials because highly explosive $AgC_2$ and $AuC_2$ would form when these anode materials are fully discharged. Note that the alkalinated transition metal acetylides are not explosive and can survive heating to 500° C. and above, and grinding as reviewed in U. Ruschewitz (2006), "Ternary Alkali Metal Transition Metal Acetylides", Zeitschrift für Anorg. Allg. Chem., 632, 705.

BRIEF SUMMARY OF THE INVENTION

In various exemplary embodiments, the present disclosure relates to battery electrodes including electroactive material made of ternary acetylides of chemical formula $A_nMC_2$, where A is alkali or alkaline-earth element; M is transition metal or metalloid element; $C_2$ is reference to the acetylide ion; n is an integer that is 0, 1, 2, 3 or 4 when A is an alkali element, and 0, 1, or 2 when A is an alkaline-earth element. The ternary acetylides of $A_nMC_2$ chemical formula having one-dimensional polymeric substructures composed of $[MC_2]$ repeating units whereby acetylide ions link neighboring M atoms. The one-dimensional polymeric substructures are embedded in a matrix of alkali and/or alkaline-earth elements. The electroactive material has an overall stoichiometry that may be an arbitrary combination of several possible $A_nMC_2$ stoichiometries. In the fully discharged form, the electroactive material contains sufficient amount of A atoms in the matrix to avoid the formation of potentially explosive $MC_2$ acetylides. The battery anode including $A_nMC_2$ ternary acetylides may have a more negative electrode potential than bulk metallic lithium, for certain compositions. Battery electrodes including $A_nMC_2$ ternary acetylides exhibit high charge/discharge capacities due to the ease of diffusion of cations along the one-dimensional polymeric substructures.

In an exemplary embodiment, a novel intercalation electrode material includes ternary acetylides of chemical formula $A_nMC_2$, where A is alkali or alkaline-earth element; M is transition metal or metalloid element; $C_2$ is reference to an acetylide ion; n is an integer that is 1, 2, 3 or 4 when A is alkali element and 1 or 2 when A is alkaline-earth element. The alkali elements can include one of Lithium (Li), Sodium (Na), Potassium (K), Rubidium (Rb), Cesium (Cs) and Francium (Fr). The alkaline-earth elements can include one of Berilium (Be), Magnesium (Mg), Calcium (Ca), Strontium (Sr), Barium (Ba), and Radium (Ra). M can be a transition metal that is any element in groups 3 through 12 inclusive on the Periodic Table of Elements. M can be a metalloid element selected from the following group of elements: Tellurium (Te), Selenium (Se), Arsenic (As), Antimony (Sb), Bismuth (Bi), Carbon (C), Silicon (Si), Germanium (Ge), Tin (Sn), Lead (Pb), Boron (B), Aluminum (Al), Gallium (Ga), Indium (In), and Thallium (Tl). M can be one of Copper (Cu), Nickel (Ni), Iron (Fe), Zinc (Zn), Cobalt (Co), Manganese (Mn), Chromium (Cr), Vanadium (V), or Titanium (T). The alkali metal can include one of lithium, sodium, potassium, rubidium, and cesium; and wherein the transition metal can be represented by elements 21 (Sc) to 30 (Zn). The novel intercalation electrode material can retain at least one alkali or alkaline-earth atom per $C_2$ unit in the discharged state of a battery.

In another exemplary embodiment, negative electrode materials composed of ternary acetylides with compositions include one of $Li_2MC_2$, $Na_2MC_2$, $K_2MC_2$, $LiMgMC_2$, $NaMgMC_2$, and $KMgMC_2$, where M is a transition metal represented by elements 21 to 30, in the fully charged state of the battery.

In yet another exemplary embodiment, a battery includes an electrode formed with a material including ternary acetylides of chemical formula: $A_nMC_2$, where A is alkali or alkaline-earth element; M is transition metal or metalloid element; $C_2$ is reference to an acetylide ion; n is an integer that is 0, 1, 2, 3 or 4 when A is alkali element and 0, 1, or 2 when A is alkaline-earth element. Optionally, the electrode includes an anode; and wherein the material includes a unique rod-like substructure allowing for geometrically unhindered traffic of alkali ions thereby providing intercalation of extra alkali ions. Alternatively, the electrode includes an cathode with M having oxidation numbers of 0 or +1 only and M having high electronegativity.

BRIEF DESCRIPTION OF THE DRAWING(S)

Exemplary and non-limiting embodiments of the present disclosure are illustrated and described herein with reference to various drawings (in some of the drawings following similar diagrams from U. Ruschewitz (2006), "Ternary Alkali Metal Transition Metal Acetylides", Zeitschrift für Anorg. Allg. Chem., 632, 705.), in which like reference numbers denote like method steps and/or system components, respectively, and in which.

DETAILED DESCRIPTION OF THE INVENTION

In various exemplary embodiments, ternary acetylide compounds are described which can be safely used as electrode materials. The ternary acetylides can also be used as electroactive materials in Na and K intercalation batteries. Furthermore, it is shown that some of the ternary acetylide compounds have more negative electrode potentials when used as anodes (during discharge) than bulk metallic lithium, which allows for a significantly improved energy storage capacity as compared to the same cell at an anode potential identical with that of bulk metallic Lithium. Ternary acetylide electrode materials are also advantageous for their high charge/discharge capacities due to the ease of diffusion of cations along isolated one-dimensional negatively charged polymeric subunits with repeating unit of $[MC_2]$.

In an exemplary embodiment, battery electrodes include electroactive material made of ternary acetylides of chemical formula $A_nMC_2$, where A is alkali or alkaline-earth element; M is transition metal or metalloid element; $C_2$ is reference to the acetylide ion; n is an integer that is 0, 1, 2, 3 or 4 when A is alkali element and 0, 1, or 2 when A is alkaline-earth element. The ternary acetylides of $A_nMC_2$ chemical formula having one-dimensional polymeric substructures composed of $[MC_2]$ repeating units whereby acetylide ions link neighboring M atoms. The one-dimensional polymeric substructures are embedded in a matrix of alkali and/or alkaline-earth elements. The electroactive material has an overall stoichiometry that may be an arbitrary combination of several possible $A_nMC_2$ stoichiometries. In the fully discharged form, the electroactive material contains sufficient amount of A atoms to avoid the formation of explosive $MC_2$ acetylides. The battery anode including $A_nMC_2$ ternary acetylides may have a more negative electrode potential than bulk metallic lithium, for certain compositions. Battery electrodes including $A_nMC_2$ ternary acetylides exhibit high charge/discharge capacities due to the ease of diffusion of cations along the one-dimensional polymeric substructures.

The ternary acetylides of $A_nMC_2$ chemical formula were investigated for applications related to photocathodes. This work is described in co-pending U.S. Application "LOW-WORKFUNCTION PHOTOCATHODES BASED ON ACETYLIDE COMPOUNDS" and in a scientific publication in Physical Review B 86, 035142 (2012) entitled "Anomalous Workfunction Anisotropy in Ternary Acetylides", by the present inventors, the contents of which are incorporated by reference herein. This class of materials has the remarkable and unique structural property that it consists of $[MC_2]_\infty$ linear chains embedded into an alkali metal matrix.

This atomic arrangement is especially suited for an unhindered traffic of alkali ions along the $[MC_2]_\infty$ chains, a favorable property for alkali-ion intercalation electrodes. Furthermore, the alkali atoms are relative weakly bound in this system, as they are weakly chelated and electrostatically bound to the $C_2^{2-}$ (acetylide) anions. When n=2, the oxidation number of the "M" atoms is 0 (zero), when n=1, the oxidation number of "M" is +1 (plus one). As both n=1 and n=2 structures have been synthesized and their structures measured, it is reasonable to assume that the n=1 and n=2 variants represent the empty and alkali-intercalated forms of a material that behaves analogously to typical Li-ion intercalation systems. Further inspection of the crystal structure and corresponding theoretical calculations using standard Density Functional Theory codes reveal that many ternary acetylides can accommodate as much as 4 alkali cations per unit cell, when the $[MC2]_\infty$ chains are in a hexagonal packing arrangement. One example of such theoretically designed systems is $Li_4CuC_2$ Considering the above described uniqueness of the crystal-structure and its consequences for geometrically unhindered alkali-ion diffusion, these materials represent a unique class of materials for intercalation electrode applications, both as anodes and as cathodes, in different oxidation states.

These new materials could be used analogously to other known Li-ion intercalation materials, in nanocrystalline form. Actually, the material can also be considered to be an analogue of graphite intercalating Li, but in this case the carbonic material is not 2-dimensional as in the case of graphite, instead it is 1-dimensional thus allowing for an easier adaptation of the crystal structure to alkali ion diffusion.

Battery Electrode

The battery electrode is made of a composite material. The composite material includes nanometer and micrometer sized particles of the electroactive material embedded in a porous conductive matrix, typically made of porous carbon, supporting electrolyte, and a binder material, such as polyvinylidene fluoride.

Electroactive Material

The electroactive material includes ternary acetylides of chemical formula $A_nMC_2$, where A is alkali or alkaline-earth element; M is transition metal or metalloid element; $C_2$ is reference to the acetylide ion; n is an integer that is 0, 1, 2, 3 or 4 when A is alkali element and 1 or 2 when A is alkaline-earth element.

$A_nMC_2$ is preferably created by reacting crystalline $A_nM$ with gaseous acetylene—$C_2H_2$. Alternatively, $A_nMC_2$ is preferably created by reacting crystalline (solid) $AC_2$ with fine powder crystalline (solid) M such as reviewed in U. Ruschewitz (2006), "Ternary Alkali Metal Transition Metal Acetylides", Zeitschrift für Anorg. Allg. Chem., 632, 705.

The alkali elements are Lithium (Li), Sodium (Na), Potassium (K), Rubidium (Rb), Cesium (Cs) and Francium (Fr). The alkaline-earth elements are Berilium (Be), Magnesium (Mg), Calcium (Ca), Strontium (Sr), Barium (Ba), and Radium (Ra). The preferred elements are alkali—Li, Na, and K.

M is a transition metal that is any element in groups 3 through 12 inclusive on the Periodic Table of Elements (elements 21 (Sc) to 30 (Zn)). In another exemplary embodiment, M is a metalloid element selected from the following group of elements: Tellurium (Te), Selenium (Se), Arsenic (As), Antimony (Sb), Bismuth (Bi), Carbon (C), Silicon (Si), Germanium (Ge), Tin (Sn), Lead (Pb), Boron (B), Aluminum (Al), Gallium (Ga), Indium (In), and Thallium (Tl). In some preferred embodiments, M is Copper (Cu), Nickel (Ni), Iron (Fe), Zinc (Zn), Cobalt (Co), Manganese (Mn), Chromium (Cr), Vanadium (V) or Titanium (T).

The ternary acetylides of $A_nMC_2$ chemical formula having one-dimensional polymeric substructures composed of $[MC_2]$ repeating units whereby acetylide ions link neighboring M atoms. The one-dimensional polymeric substructures are embedded in a matrix of alkali and/or alkaline-earth elements. The electroactive material has an overall stoichiometry that may be an arbitrary combination of several possible $A_nMC_2$ stoichiometries.

In the fully discharged form, the electroactive material contains sufficient amount of A atoms to avoid the formation of explosive $MC_2$ acetylides. Such an excess amount of A atoms also contributes to an increased electrical conductivity of the electroactive material. In a preferred embodiment the discharged form of the ternary acetylides would be composed of $LiMC_2$, $NaMC_2$, $KMC_2$, $MgMC_2$, with M preferably being a transition metal from the Sc—Zn row of the periodic table of the elements.

The battery electrode including $A_nMC_2$ ternary acetylides may have a more negative electrode potential than bulk metallic lithium, for certain compositions. An example of such composition is $Li_2CuC_2$. Theoretical calculations based on density functional theory using the Perdew-Burke-Ernzerhof functional (J. P. Perdew, K. Burke, M. Ernzerhof, (1996), "Generalized Gradient Approximation Made Simple", Physical Review Letters, 77, 3865) and intercalation potential calculation (as described in F. Zhou, et al. (2005), "The Li intercalation potential of $LiMPO_4$ and $LiMSiO_4$ olivines with M=Fe, Mn, Co, Ni", Electrochemistry Communications, 6, 1144) predict that the intercalation of the second Li per $Li_2CuC_2$ formula unit happens at an electrode potential that is by 0.36 eV more negative than that of bulk metallic Lithium. The calculations used the Quantum Espresso suite of programs (P. Giannozzi, et. al (2009), "QUANTUM ESPRESSO: a modular and open-source software project for quantum simulations of materials", Journal of Physics: Condensed Matter, 39, 395502; www.quantum-espresso.org). A 14×14×14 k-space discretization was used, along with Marzari-Vanderbilt smearing (of 0.03 Rydberg broadness factor), a wavefunction-cutoff of 40 Rydbergs, no spin-polarization, together with pseudopotentials of Cu.pbe-d-rrk-jus.UPF, Li.pbe-n-van.UPF, C.pbe-rrkjus.UPF following Quantum Espresso notations. Unit cell parameters and atomic positions were relaxed until residual forces on atomic positions were smaller than 0.0001 Rydberg/bohr and residual stress smaller then 0.1 kbar. The unit cell enthalpies of the relaxed structures were −113.850809, −112.06584459 and −3.62318261 Rydbergs for $Li_2CuC_2$, $LiCuC_2$ and two-atomic metallic Li cells, respectively, resulting in an intercalation potential of 0.026626 (=−113.850809−(−112.065844−3.62318/2)) Rydbergs, which is equivalent to 0.362 V stronger reductive electrode potential than that of bulk metallic Lithium. This stronger reductive potential may be associated with the lengthening of the acetylide triple bond from 1.258 to 1.289 Angstroms upon Li intercalation, indicating the storage of extra negative electrons on the antibonding orbitals of the acetylide unit. The stronger-than-bulk-Li reductive potential of $Li_2CuC_2$ may thus be associated with electrons stored on the antibonding orbitals of the acetylide unit, i.e. such an acetylide unit has a stronger reducing power than bulk metallic Lithium. The higher the Li or alkali/alkaline-earth content of the unit cell is, the higher the likelihood of the ternary acetylide exhibiting a stronger-than-bulk-Li reduction potential and thus behaving as a "super anode".

Electrode potentials more negative than that of bulk metallic Lithium can greatly increase the voltage of the battery as compared to anodes with the electrode potential of bulk metallic Lithium or lower and lead to significantly increased energy storage capacity.

Battery electrodes including $A_nMC_2$ ternary acetylides exhibit high charge/discharge capacities due to the ease of diffusion of cations along the one-dimensional polymeric substructures.

Figure 1:
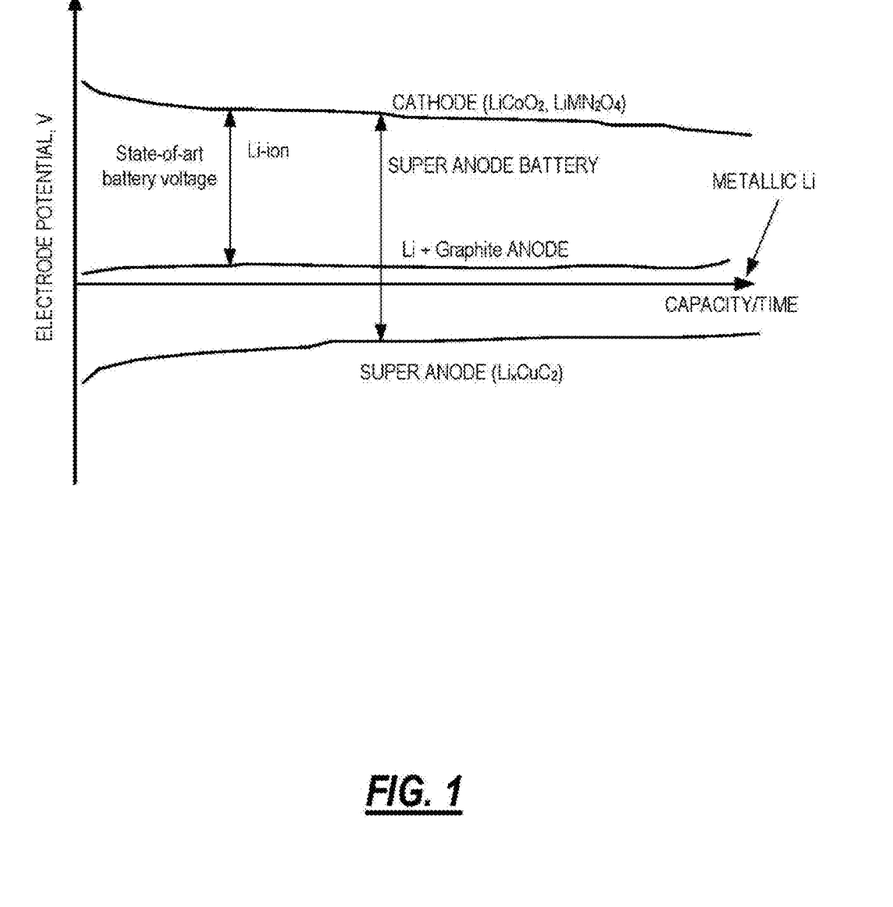
FIG. 1 is a graph of electrode potential over time for conventional Li-ion compared to a super anode construction of the present disclosure, super anodes have more negative electrode potentials than bulk metallic lithium; also note that Li2CuC2 is merely one possible example of "super anode" materials while many other materials may exhibit "super anode" properties, either ternary acetylides or other materials.

FIG. 1 is a graph of electrode potential over time for conventional Li-ion compared to a super anode construction of the present disclosure using $Li_1CuC_2$ for the super anode. That is, the $A_nMC_2$ ternary acetylides can form an entirely new class of electrode (anode) materials for Li batteries. This is due to the unique open channels, i.e. the 1-dimensional structure of the $A_nMC_2$ class of components. As shown in FIG. 1, the super anode using $Li_xCuC_2$ can provide significant improvement versus conventional anodes such as with Li and graphite.

Figure 2:
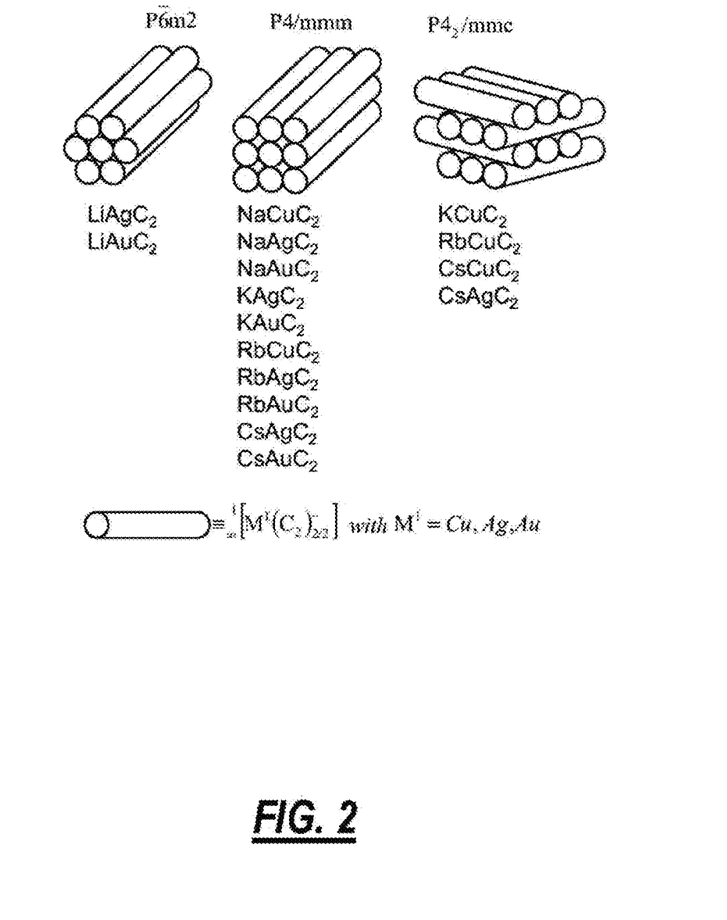
FIG. 2 is a diagram of crystal structures of ternary acetylides of composition $AM^1C_2$ where A is an alkali metal and $M^1$ is Cu, Ag, Au.
Figure 3:
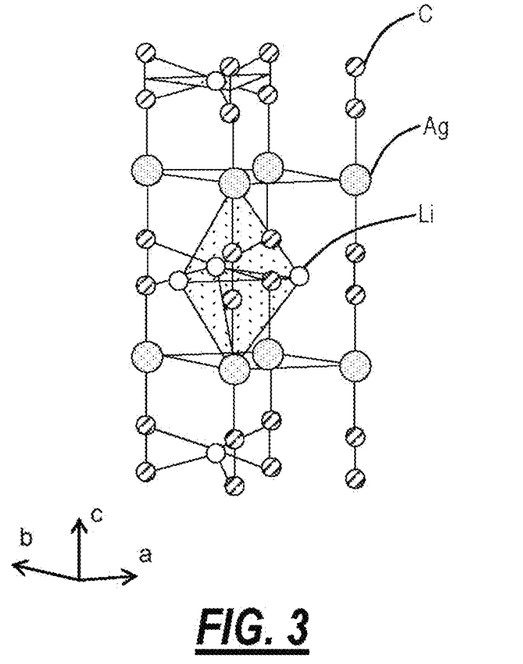
FIG. 3 is a diagram if a crystal structure of $LiAgC_2$.
Figure 4:
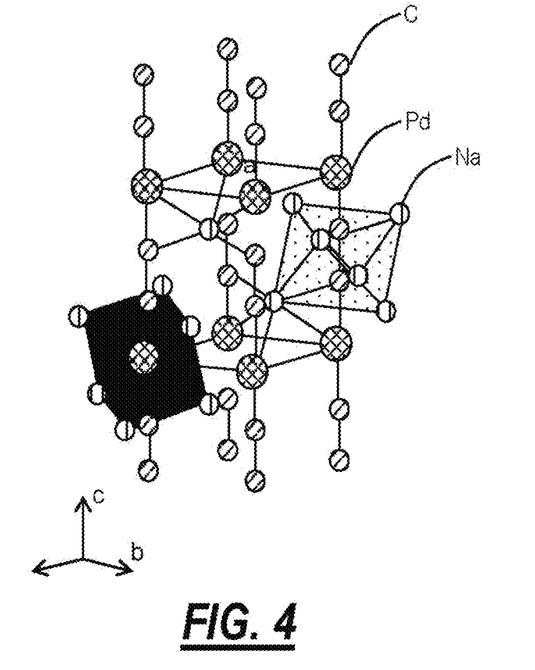
FIG. 4 is a diagram if a crystal structure of $Na_2PdC_2$.

FIG. 2 is a diagram of crystal structures of ternary acetylides of composition $AM^1C_2$ where A is an alkali metal and M' is Cu, Ag, Au showing simple rod packings. Specifically, FIG. 2 shows the ternary acetylides with one alkali ion per unit cell. FIG. 3 is a diagram if a crystal structure of $LiAgC_2$ and FIG. 4 is a diagram if a crystal structure of $Na_2PdC_2$. FIGS. 3 and 4 show structural changes due to the addition of a second alkali ion.

Figure 5:
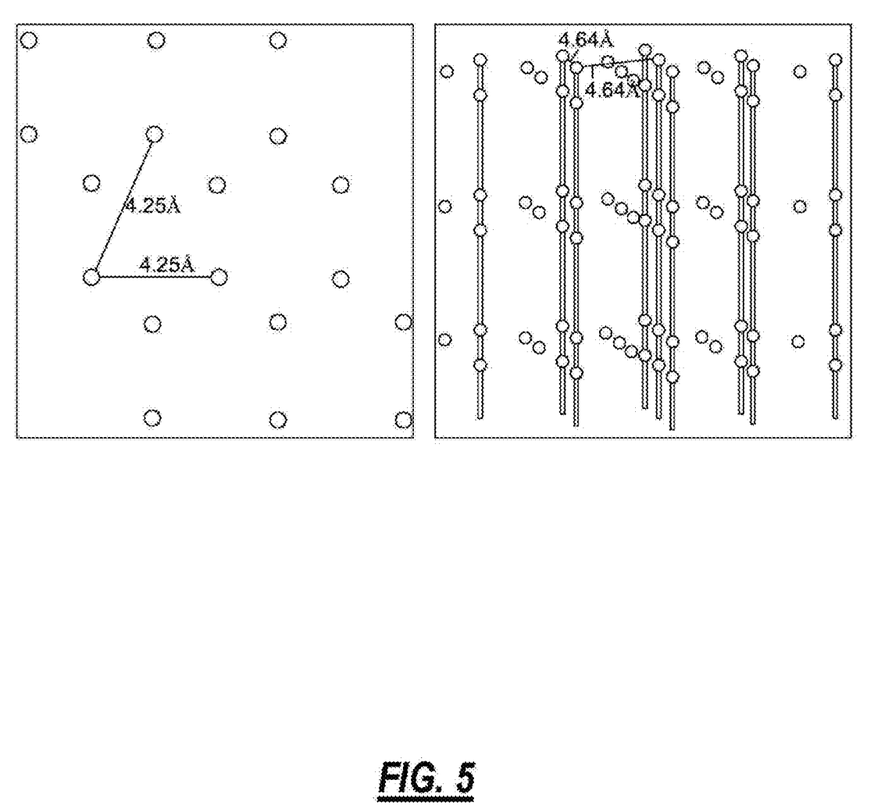
FIG. 5 is a diagram of $LiCuC_2$ Space group (P –6 m 2), as viewed along the rod-like $CuC_2$ units and sidewise.
Figure 6:
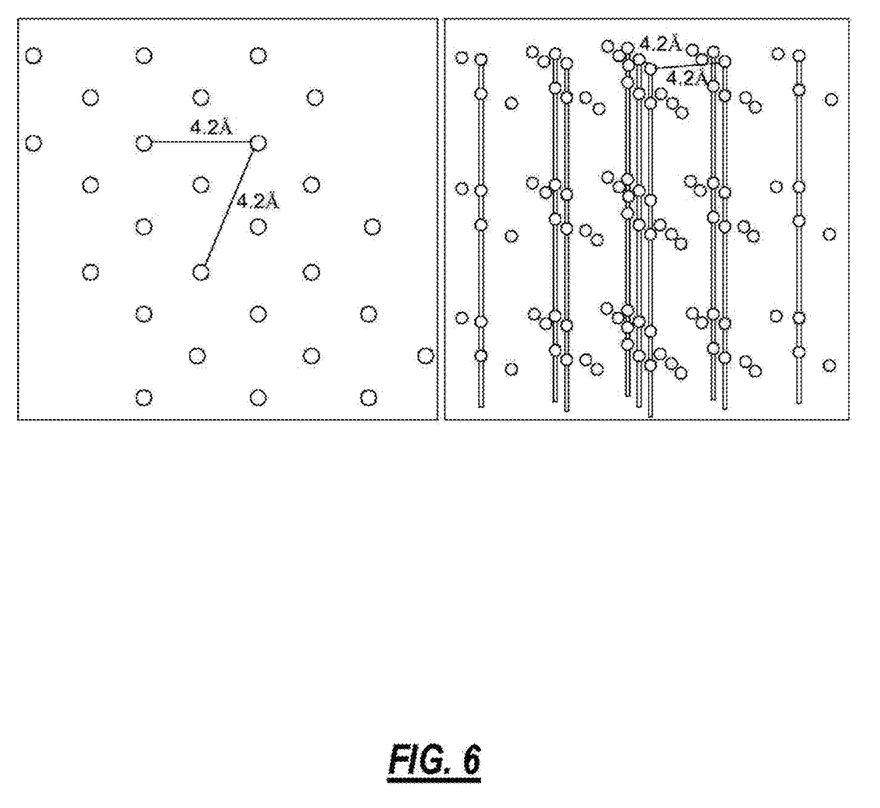
FIG. 6 is a diagram of $Li_2CuC_2$ Space group (P –3 m 1), as viewed along the rod-like $CuC_2$ units and sidewise.
Figure 7:
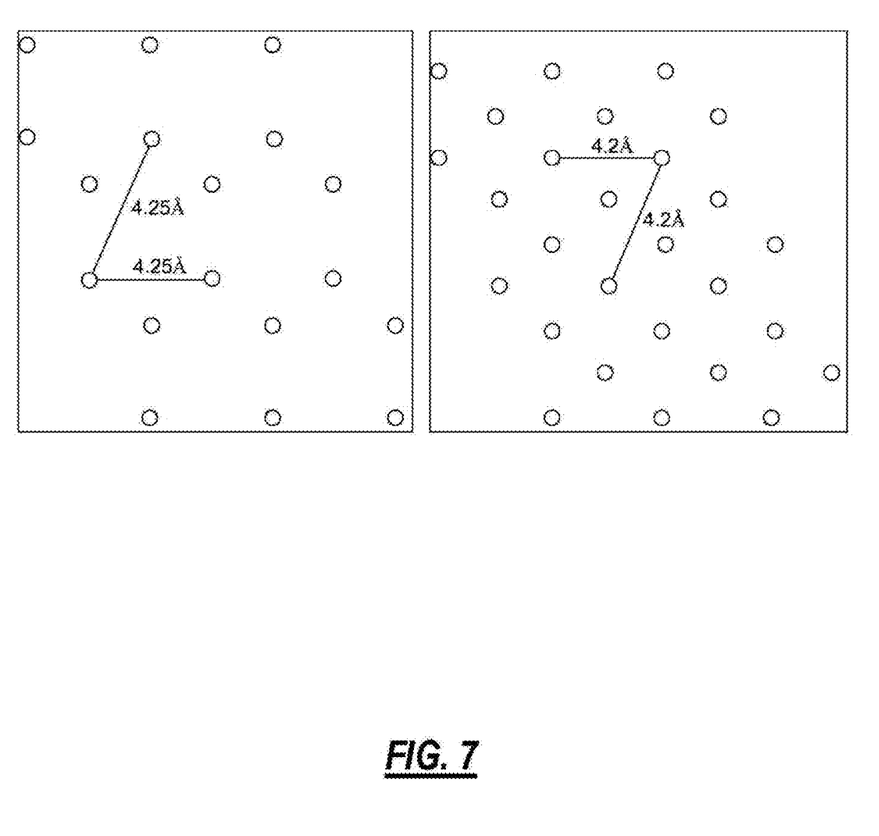
FIG. 7 is a diagram of Li intercalated into the empty hexagonal positions of $LiCuC_2$, as viewed along the rod-like $CuC_2$ units.

FIG. 5 is a diagram of $LiCuC_2$ Space group (P −6 m 2). FIG. 6 is a diagram of $Li_2CuC_2$ Space group (P −3 m 1). Li intercalated into empty hexagonal positions of LiCuC$_2$ requires about 2.2 eV energy input (DFT-calc.). This provides a stronger reducing agent, i.e. a super anode, relative to metallic Li. FIG. 7 is a diagram of Li intercalated into the empty hexagonal positions of LiCuC$_2$. The intercalation of the second Li requires 0.36 eV energy input.

In an exemplary embodiment, a battery includes an electrode formed with a material including ternary acetylides of chemical formula: A$_n$MC$_2$, where A is alkali or alkaline-earth element; M is transition metal or metalloid element; C$_2$ is reference to an acetylide ion (C$_2^{2-}$); n is an integer that is 0, 1, 2, 3 or 4 when A is alkali element and 0, 1, or 2 when A is alkaline-earth element. Optionally, the electrode includes an anode; and wherein the material includes a unique rod-like substructure allowing for geometrically unhindered traffic of alkali ions thereby providing intercalation of extra alkali ions.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure and are intended to be covered by the following claims.

What is claimed is:

1. A novel intercalation electrode material comprising ternary acetylides of chemical formula:

A$_n$MC$_2$, where A is alkali or alkaline-earth element; M is transition metal or metalloid element; C$_2$ is reference to an acetylide ion; n is an integer that is 0, 1, 2, 3 or 4 when A is alkali element and 0, 1, or 2 when A is alkaline-earth element.

2. The novel intercalation electrode material of claim 1, wherein the alkali elements comprise one of Lithium (Li), Sodium (Na), Potassium (K), Rubidium (Rb), Cesium (Cs) and Francium (Fr).

3. The novel intercalation electrode material of claim 1, wherein the alkaline-earth elements comprise one of Berilium (Be), Magnesium (Mg), Calcium (Ca), Strontium (Sr), Barium (Ba), and Radium (Ra).

4. The novel intercalation electrode material of claim 1, wherein M is a transition metal that is any element in groups 3 through 12 inclusive on the Periodic Table of Elements.

5. The novel intercalation electrode material of claim 1, wherein M is a metalloid element selected from the following group of elements:

Tellurium (Te), Selenium (Se), Arsenic (As), Antimony (Sb), Bismuth (Bi), Carbon (C), Silicon (Si), Germanium (Ge), Tin (Sn), Lead (Pb), Boron (B), Aluminum (Al), Gallium (Ga), Indium (In), and Thallium (Tl).

6. The novel intercalation electrode material of claim 1, wherein M is Copper (Cu).

7. The novel intercalation electrode material of claim 1, wherein M is Nickel (Ni).

8. The novel intercalation electrode material of claim 1, wherein M is Iron (Fe).

9. The novel intercalation electrode material of claim 1, wherein M is Zinc (Zn).

10. The novel intercalation electrode material of claim 1, wherein M is Cobalt (Co).

11. The novel intercalation electrode material of claim 1, wherein M is Manganese (Mn).

12. The novel intercalation electrode material of claim 1, wherein M is Chromium (Cr).

13. The novel intercalation electrode material of claim 1, wherein M is Vanadium (V).

14. The novel intercalation electrode material of claim 1, wherein M is Titanium (T).

15. The novel intercalation electrode material of claim 1, wherein the alkali metal comprises one of lithium, sodium, potassium, rubidium, and cesium; and wherein the transition metal is represented by elements 21 (Sc) to 30 (Zn).

16. The novel intercalation electrode material of claim 1, wherein the novel intercalation electrode material retaining at least one alkali or alkali earth atom per C$_2$ unit in the discharged state of a battery.

17. Electrode materials composed of ternary acetylides with compositions comprising one of Li$_2$MC$_2$, Na$_2$MC$_2$, K$_2$MC$_2$, LiMgMC$_2$, NaMgMC$_2$, and KMgMC$_2$, where M is a transition metal represented by elements 21 to 30, in the fully charged state of the battery.

18. A battery, comprising:

an electrode formed with a material comprising ternary acetylides of chemical formula:

A$_n$MC$_2$, where A is alkali or alkaline-earth element; M is transition metal or metalloid element; C$_2$ is reference to an acetylide ion; n is an integer that is 0, 1, 2, 3 or 4 when A is alkali element and 0, 1, or 2 when A is alkaline-earth element.

19. The battery of claim 18, wherein the electrode comprises an anode; and wherein the material comprises a unique rod-like substructure allowing for geometrically unhindered traffic of alkali ions thereby providing intercalation of extra alkali ions.

20. The battery of claim 18, wherein the electroactive material ternary acetylide has a stronger reducing electrode potential than bulk metallic lithium and is applied in the negative electrode.

* * * * *